(12) United States Patent
Elbashir et al.

(10) Patent No.: US 12,060,325 B2
(45) Date of Patent: Aug. 13, 2024

(54) METHODS OF PRODUCING DIMETHYL CARBONATE

(71) Applicant: Qatar Foundation for Education, Science and Community Development, Doha (QA)

(72) Inventors: Nimir O. Elbashir, Doha (QA); Hanif Ahmed Choudhury, Doha (QA); Mohamedsufiyan Azizurrehman Challiwala, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 0 days.

(21) Appl. No.: 17/786,871

(22) PCT Filed: Jul. 29, 2020

(86) PCT No.: PCT/QA2020/050010
§ 371 (c)(1),
(2) Date: Jun. 17, 2022

(87) PCT Pub. No.: WO2021/125989
PCT Pub. Date: Jun. 24, 2021

(65) Prior Publication Data
US 2023/0024976 A1 Jan. 26, 2023

Related U.S. Application Data

(60) Provisional application No. 62/949,139, filed on Dec. 17, 2019.

(51) Int. Cl.
C07C 68/04 (2006.01)
C07C 29/152 (2006.01)
C07C 68/08 (2006.01)

(52) U.S. Cl.
CPC ............ *C07C 68/04* (2013.01); *C07C 29/152* (2013.01); *C07C 68/08* (2013.01)

(58) Field of Classification Search
CPC .................................................. C07C 68/04
See application file for complete search history.

(56) References Cited

U.S. PATENT DOCUMENTS

| 5,523,452 A * | 6/1996 | Kricsfalussy | ........... C07C 68/01 |
| | | | 558/277 |
| 7,790,914 B2 * | 9/2010 | Osora | .................... B01J 27/053 |
| | | | 558/277 |

FOREIGN PATENT DOCUMENTS

| CN | 109647497 A | 4/2019 |
| CN | 110479287 A | 11/2019 |

OTHER PUBLICATIONS

International Search Report for related International Application No. PCT/QA2020/050010; action dated Jun. 24, 2021; (2 pages).
Written Opinion for related International Application No. PCT/QA2020/050010; action dated Jun. 24, 2021; (6 pages).
Bansode, et al. "Continuous DMC Synthesis from CO2 and Methanol over a CeO2 Catalyst in a Fixed Bed Reactor in the Presence of a Dehydrating Agent"; Abstract; p. 3878, figure 1; p. 3879, col. 1, first-second paragraph; American Chemical Society Catalysis; Jul. 29, 2015.
Hu, et al; "Analysis of direct synthesis of dimethyl carbonate from methanol and CO2 intensified by in-situ hydration-assisted reactive distillation with side reactor"; abstract; p. 109, col. 2, second paragraph; p. 110, col. 1, second-third paragraphs; p. 110 column 2, figure 1; p. 112, col. 1, third-fourth paragraphs; p. 114, col. 1, figures 6c and 7b; p. 115, col. 1, table 3 and figure 10; Chemical Engineering & Processing; Jul. 2018.
Office Action for related Chinese Application No. 202080093237.2; action dated Dec. 22, 2023; (13 pages).

* cited by examiner

*Primary Examiner* — Golam M Shameem
(74) *Attorney, Agent, or Firm* — K&L Gates LLP

(57) ABSTRACT

Disclosed is a high yield, high selectivity and high conversion method to produce Dimethyl Carbonate (DMC) from carbon dioxide ($CO_2$) and methanol (MeOH) using optimized concentration of ethylene oxide as water scavenger. The method provides an alternative and optimized solution towards the problem of formation of water in DMC synthesis by reporting optimal feed ratio and scavenger to MeOH feed ratio. The disclosure also discloses an optimal pressure condition that could have significant impact on economy of compression of the feed to the DMC reactor.

17 Claims, 6 Drawing Sheets

METHODS OF PRODUCING DIMETHYL CARBONATE

PRIORITY

The present application claims priority to U.S. Ser. No. 62/949,139, filed Dec. 17, 2019, the entire contents of which are being incorporated herein by reference.

BACKGROUND

Dimethyl Carbonate (DMC) is considered as a green chemical because of its low toxicity for humans and other life forms. DMC is the simplest organic carbonate that has great importance as a fuel additive, solvent and reactant. DMC has good solvency power, low viscosity and low toxicity, which makes it a viable alternative as solvent. DMC is also considered as an alternate for several toxic compounds like ketones, acetate esters and solvents used for paints. Additionally, one of the trending uses of DMC is as an electrolyte in lithium rechargeable batteries. DMC is also used as building blocks for many organic syntheses such as methylation reaction and carbonylation. DMC is also used in methoxy-carbonylation reactions to prepare, such as phenylethenyl methyl carbonate, from phenyl acetaldehyde.

DMC is a colorless, flammable and transparent liquid which has been recommended as alternative fuel or oxygenated additive fuels for combustion engines. DMC has several features that make it an attractive candidate as additive for fuel. DMC is non-corrosive, safe to handle, high oxygen content (54% by weight), high miscibility in fossil fuel, high hydrogen to carbon (H/C) ratio, low boiling (eases in spray atomization and mixing), help reduce soot formation during combustion. Additionally, DMC can improve the octane rating of the gasoline. DMC also has higher density (1.069 g/cm3) than Gas to liquid (GTL) fuels (0.7 g/cm3) and can also be used as additive to enhance the density of GTL fuels.

DMC has several blending properties that helps the GTL fuel to meet the American Standard of Testing and Materials guidelines (D4814-19). For example, it has a high research octane number of 101-106, high oxygen content and low Reid vapor pressure (RVP) that are desirable for an ideal gasoline fuel. DMC blended fuel also has less carbon monoxide (CO), Nitrogen oxides (NOx) and Sulphur oxides (SOx) emission.

Direct synthesis of DMC from carbon dioxide ($CO_2$) and methanol (MeOH) is one of the many attractive pathways of utilizing carbon dioxide ($CO_2$) while producing value added products. However, this reaction is plagued by extensive thermodynamic limitations that result in low selectivity and yield of DMC as a desirable product. Following chemical equation provides stoichiometry of the direct synthesis reaction:

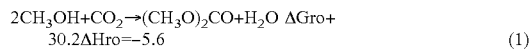

$$2CH_3OH + CO_2 \rightarrow (CH_3O)_2CO + H_2O \quad \Delta G{ro} + 30.2 \Delta H{ro} = -5.6 \quad (1)$$

The most favorable conditions identified for this reaction pertain to high pressure (greater than 50 bar) and low temperature (less than 100° C.) resulting in high direct and indirect production costs due to separation and recycle in addition to feed compression. Due to these challenges, economics related to direct synthesis route have always been marred with contention for commercialization if compared to conventional synthesis routes.

In the past, DMC was synthesized using numerous techniques such as (i) transesterification of urea, ethylene carbonate (ii) methanol oxy-carbonylation, (iii) methyl nitrite carbonylation, (iv) methanol phosgenation. However, due to the toxic nature of phosgene, alternative reaction scheme were developed by many industries worldwide [1]. At present, DMC is produced by many chemical companies in the world such as General Electric, SNPE, Texaco, Mitsubishi, and BASF with their complex patented process.

Compared to other routes stated above, the direct synthesis reaction from $CO_2$ and MeOH had only recently gained traction due to its environmentally benign nature of utilizing $CO_2$ while upgrading MeOH as a fuel additive. Additionally, this reaction is highly sustainable route that eliminates utilization of toxic chemicals and feedstocks like phosgene and CO. The challenge is the economic feasibility of this reaction due to thermodynamic limitation stated earlier in this section. It is mainly due to chemical inertness of $CO_2$ resulting in high energy requirements for its activation. Various heterogeneous catalyst such as $ZrO_2$, $SiO_2$, $TiO_2$, H-ZSM-5, H-USY, H-MOR, ZnO, $MoO_3$, $Bi_2O_3$, MgO, $Y_2O_3$, $HfO_2$, $La_2O_3$, $Pr_6O_{11}$, $Ga_2O_3$, $GeO_2$, $In_2O_3$, and $Sb_2O_3$[1] has been reported to give DMC selectivity for direct synthesis as per Eq. 1. However, these catalytic systems have been shown to give DMC yield <1% and selectivity ranging from 60-90%. It has been reported that even under conditions of high pressure, the maximum DMC yield is <1%. Therefore enhancing the DMC yield in direct synthesis as given in Eq. 1 will require utilization of other engineering technique such as in situ removal of the byproducts to shift the equilibrium and identification novel catalytic systems. Honda et al. [3] has reported the direct synthesis reaction using $CeO_2$ as catalyst and 2-cyanonpyridine (CP) as dehydrating agent. It was shown that the introduction of 2-CP as dehydrating agent leads to higher MeOH (>99%) conversion and DMC selectivity (>94%) than previously reported in literatures [4]-[12]. Bansode and Urukawa [13] also reported DMC synthesis on a $CeO_2$ catalyst using 2-CP as dehydrating agent in a flow reactor for 200 h Time On Steam (TOS). Recent study by Stoian et al. [14] reported very high MeOH conversion (>90%) and high DMC selectivity (>95%) using the 1% Gd on $CeO_2$ and solvent 2-cyanopyridine (2-CP) as dehydrating agent. They have also reported that 2-CP had beneficial effect on the catalyst activity as it retards the rates of 2-CP adoption on catalyst site thereby reducing catalyst deactivation. However their work is not industrially attractive owing to the cost and availability issues associated with the lanthanide catalyst and 2-CP. Moreover, regeneration of 2 CP from 2-Picolinamide is also complicated due to additional requirement of a selective catalyst and a separation process similar to an adsorption and separation process.

Significant efforts by the scientific community have been employed in improving catalyst performance and identification of appropriate reaction conditions, however almost no efforts have been employed in overcoming the aforementioned thermodynamic challenges that could result in better yield. There are only two broad pathways focused in the literature that circumvent thermodynamic limitations of DMC process, (i) Introduction of a chemical scavenger that traps water in-situ to push the reaction forward and (ii) Utilization of Reactive distillation (RD) technique that in-situ separates water while continuing the forward reaction.

In-situ removal of product (water) during the direct synthesis of DMC has been very effective in some cases where both yield and selectivity increased significantly. Several authors have reported successful attempts in enhancing the yield by shifting the equilibrium of direct synthesis reaction by utilizing dehydrating agents such as molecular sieves 3A Zeolite, $MgSO_4$, $Na_2SO_4$ [4].

An older process (EP0298167B1) disclosed an interesting pathway for co-production of both DMC and ethylene glycol (EG). However, a transesterification technique was utilized for the conversion reaction, in which ethylene carbonate and MeOH were reacted in the presence of several classes of heterogeneous catalysts. The catalysts were gel type ion exchange resins having tertiary functional groups of amines that are acidic along with alkaline functional group resins that facilitate the overall reaction process.

Water scavenges such as dimethoxypropane (DMP) and dicyclohexylcarbodiimide (DCC) has been reported to be very effective also for in situ removal of water and shifting the equilibrium [15]. Very recently Honda et al. [3] have reported 2-CP as effective water scavenger for direct synthesis of DMC. The authors have reported a list of nitrile compounds that were showed to have good water scavenging capacity, higher DMC yield and selectivity. Although, water scavenger exhibit higher efficacy than dehydrating agents, and give better DMC yield, practical application of the water scavengers are limited due to cost associated with regeneration of them. Additionally, utilizing the scavengers in large quantity may also incur additional burden on the process both in terms of cost and abundance. Therefore, only those water scavenger that are easily available, have lower regeneration cost compared to reported ones in the literature should be utilized for a successful process.

As an alternative, simultaneous removal of products from the reaction mixture and to shift the equilibrium, RD process has been reported previously [16]. Huang et al. [17] reported an Aspen® Plus simulation study of RD system with propylene glycol (PG) as dehydrating agent for direct synthesis of DMC. They have reported energy saving of approximately 53.8% and 31.54% of total annual cost saving. A recent study by Hu et al. [18] reported Aspen Plus simulation of RD for direct synthesis of DMC. They have used an in situ ethylene oxide (EO) assisted RD process with a gas-phase side reactor to enhance the DMC yield. Authors have reported 99.5% MeOH conversion for EO-assisted RD process.

A method to produce DMC and EG was described in CN104761429B and includes a series of steps involving use of ionic liquid composite catalyst for reaction of ethylene carbonate and $CO_2$ and then a subsequent reaction of ethylene carbonate solution with MeOH catalyst in a reactive distillation column and finally transesterification of the products to form DMC. Other byproducts are then separated and converted to glycols.

CN00364956C reported a method involving alkylene oxide, carbon dioxide and MeOH as mix feed counter currently flowing over a bed of catalyst material. The reactant gases get absorbed in the liquid phase flowing in opposite direction, while at the same time react at the catalyst surface. The reaction produces cyclic carbonate in liquid phase that gets mixed with liquid MeOH on its way down the reactor. The top and bottom temperature of the reactor/absorption column is set in such a way that separation of the products happen at different lengths of the reactor bed. In particular the inventors reported high purity of the cyclic carbonate (more than 99%) at the outlet.

CN101844986A reported a method for direct synthesis reaction of $CO_2$ and MeOH to produce DMC that included several steps involving synthesis of MeOH and its direct interaction with MeOH to produce DMC. The method also employs a RD column as a combination of rectifying section and distillation column for separation of the various reaction components. The main target was to reduce $CO_2$ emissions of water gas generated from coal furnace.

A method to co-produce DMC from MeOH and nitrite oxide (NO) was reported in CN101190884B. In this work, a pathway was reported for co-producing DMC along with dimethyl oxalate as a primary product. The method involves utilization of industrial grade 99.5% MeOH and industrial grade CO and 02 mix gas for this reaction. The production steps involve a series of reactions comprising of nitrosation, oxidative carbonylation, extraction and a rectification step.

SUMMARY

The present technology is directed to, for example, a symbiotic relationship between two reactions that happen in series and parallel mode. In particular, the reaction of MeOH and $CO_2$ leads to the formation of DMC and water as described in Eq. 1, while the reaction of water that is produced with EO leads to the formation of EG that aides in further pushing the first reaction forward and by itself supporting the second reaction. The main reason for the synergism is the high affinity of water to react with EO, which helps create an imbalance in the equilibrium and indirectly forces the first reaction to happen only in forward direction leading to high conversions and selectivity towards DMC.

In a general embodiment, the present disclosure provides a method to produce DMC, the method comprising adding to a reactor reactants comprising $CO_2$ and MeOH for a first reaction. A pressure in the reactor is from 1 bar to 100 bar, and a temperature in the reactor is from 100° C. to 200° C. The reactor operates in a continuous mode with a continuous flow of feed of the reactants into the reactor and products leaving the reactor.

In one embodiment, the $CO_2$ and the MeOH may be pressurized before or after being added to the reactor.

In one embodiment, a method of removing byproduct water, thereby increasing conversion of the feed, may include adding a water scavenger to the reactor to remove water in situ in the reactor in a second reaction.

In one embodiment, the water scavenger may comprise EO.

In one embodiment, a feed ratio of the EO to the MeOH is from about 0 to about 4.

In one embodiment, the feed ratio of the EO to the MeOH is from about 0.5 to about 4.

In one embodiment, the feed ratio of the EO to the MeOH is from about 0.5 to about 1.5.

In one embodiment, the feed ratio of the EO to the MeOH is about 1.

In one embodiment, a feed ratio of EO/MeOH/$CO_2$ (E:M:C) is about 1:1:1.

In one embodiment, the pressure in the reactor is about 10 bar. The conversion of the feed is about 85% to 92%.

In one embodiment, the pressure in the reactor is below 10 bar.

In one embodiment, the pressure in the reactor is about 5 bar.

In one embodiment, the pressure in the reactor is up to 1 bar. The conversion of the MeOH (MEOH) is greater than 65%. DMC selectivity is greater than 95%.

In one embodiment, the first reaction is $CO_2+2$ MeOH→DMC+$H_2O$.

In one embodiment, the second reaction is EO+$H_2O$→EG.

Additional features and advantages are described herein, and will be apparent from the following detailed description.

BRIEF DESCRIPTION OF THE DRAWING

Features and advantages of the present technology according to various embodiments including methods of producing DMC described herein may be better understood by reference to the accompanying drawings in which.

DETAILED DESCRIPTION

The present technology provides a high yield, high selectivity and high conversion method to produce DMC from CO$_2$ and MeOH using an optimal concentration of EO as water scavenger. The disclosed method provides an alternative and optimized solution towards the problem of formation of water in DMC synthesis using an optimal feed ratio and scavenger to MeOH feed ratio. The present disclosure also discloses an optimal pressure condition that could have significant impact on economy of compression of the feed to the DMC reactor. The present technology is directed to single reaction between MeOH and CO$_2$ to produce DMC, wherein an optimized ratio of chemical scavenger EO is utilized to trap water and convert to a more value added chemical EG.

The present technology circumvents thermodynamic barriers associated with direct synthesis of DMC process from CO$_2$ and MeOH, utilizing a MATLAB® code using well-known Gibbs Free Energy minimization (GFEM) principle. In this, the Code identifies minimal GFE of the system that corresponds to thermodynamic equilibrium. The following equation provides a general form of Gibbs Free Energy equation as a function of molar composition, temperature and pressure:

$$G^{total} = \sum_{i=1}^{N} n_i \left( \Delta G_{fi}^0 + RT \ln \left( y_i \frac{\Phi_i P}{P_o} \right) \right) \quad (2)$$

where, T: reaction temperature, P: reaction pressure, μi: chemical potential of reaction specie 'i', R: universal gas constant, $n_i$: Molar composition of reaction specie 'i', $y_i$: Equilibrium mole fraction of reaction specie 'i', $\Delta G_{fi}^0$: Standard Gibbs Free energy of formation of specie 'i', Φi: Fugacity coefficient of reaction specie 'i'.

The reaction species 'i' in this system pertain to MeOH, CO$_2$, DMC, H$_2$O, EO and EG.

Detailed procedure and various calculation steps are provided in previous publications [19], [20].

The method employed in this study pertains to the utilization of different ratios of chemical scavenger to MeOH and CO$_2$ and identifying its impact on overall yield and selectivity of DMC while maximizing CO$_2$ and MeOH conversion. The objective function targets maximizing DMC yield.

Figure 1:
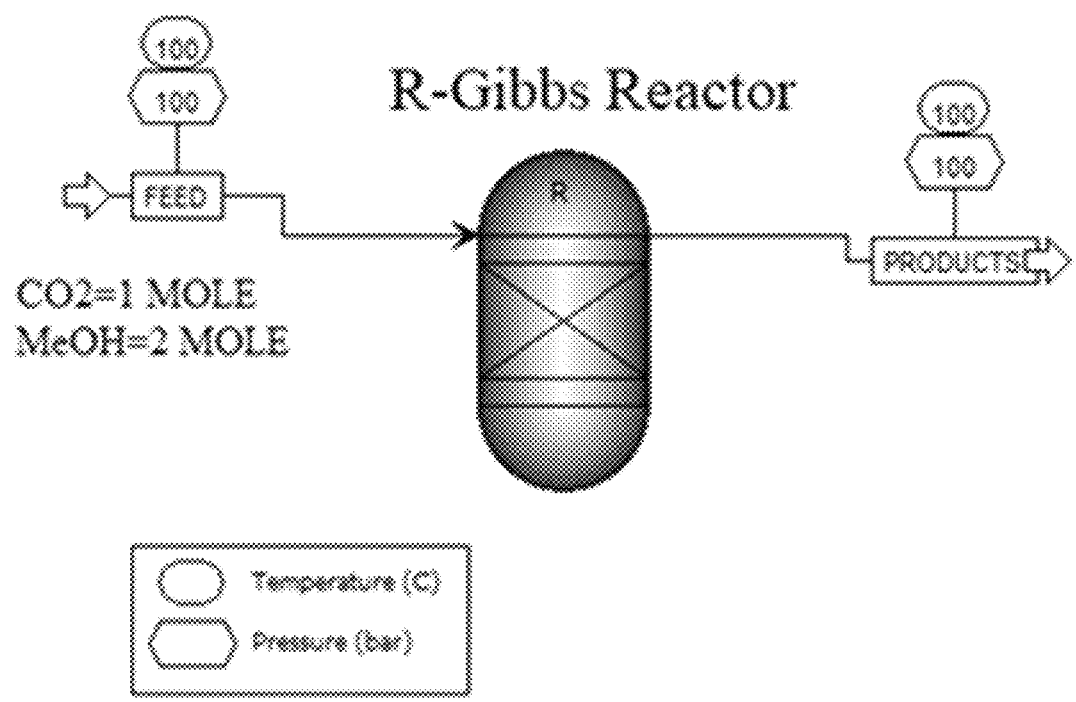
FIG. 1 shows the ASPEN® Plus simulation of Gibbs reactor to estimate thermodynamic equilibrium composition at MeOH:CO$_2$ (M:C) feed ratio of 2:1 at 100° C. temperature and 100 bar pressure.

The developed MATLAB® model results were validated with ASPEN® Plus process simulator results in which we used R-Gibbs reactor for simulating the proposed reaction system. ASPEN® Plus process flowsheet with the R-Gibbs reactor is provided in FIG. 1. In ASPEN® simulation, the system comprised of CO$_2$, MeOH, DMC and water as reaction components, while the system temperature was set to 100° C. at 100 bar pressure. In R-Gibbs reactor settings, we only allowed vapor and liquid as valid phases, as formation of solid is not feasible in this process. Simulation was conducted at stoichiometric feed composition of MeOH to CO$_2$ (M:C) ratio of 2:1. Similar operational and feed conditions were maintained in MATLAB® simulation to avoid any discrepancy between the results of the two softwares. Table 1 provides side by side comparison between our results generated from MATLAB® model, and the ASPEN® plus process simulator. It can be observed that the equilibrium composition of all the species agrees well with ASPEN® Plus data suggesting credibility of the developed MATLAB® model for such assessments. Complex optimization routines could be easily implemented on MATLAB® scripts which are not possible on process simulators.

The pathway of the reaction is between MeOH and CO$_2$ to produce DMC and water, while the reaction is aided by the presence of water scavenger EO. EO reacts with water to produce EG. This technology requires a single reactor unit for the entire operation. Water acts as an intermediate as a series-parallel reaction happens, and water reacts with ethylene oxide to form ethylene glycol. Role of EO is to improve the selectivity of DMC by removing water to produce EG. Any commercial catalyst can be used.

As non-limiting examples, the EO:MeOH (E:M) ratio in the disclosed reaction can be from 0.25 to 1.25 over a range of temperature from 100° C. to 200° C. at 1 bar to 100 bar pressure. The ratio of CO$_2$ to MeOH can be in the range of 1 to 4.

The disclosed technology could be used to replace the existing chemical processes to produce DMC as it is more sustainable as a single step. Additionally, this process could also be an alternative pathway for EG production since the EG is the main byproduct of this novel process.

The present technology uses the thermodynamics Le' Chatelier's principal to further the production of DMC that was limited by the co-product water. The technology continuously remove water by its series-parallel reaction with EO to produce EG. The technology utilizes the synergy between two separate reactions: $CO_{2+2}$ MeOH→DMC+$H_2O$ and EO+$H_2O$→EG to improve the selectivity of the desired DMC product.

The present technology has extremely high conversion, for example, >90% of MeOH and >90% of DMC selectivity, and throughput per pass at optimal conditions.

The disclosed technology has at least the following benefits:
1) Direct conversion of $CO_2$ and MeOH to DMC, rather than utilization of expensive and more toxic/poisonous chemicals,
2) Single step and single reactor process,
3) Presents an alternative pathway for EG production,
4) Offers high selectivity and conversion toward DMC and
5) Operates at low pressure (1-10 bar), which is not possible in the conventional processes for DMC production.

In the disclosed reaction, an optimal feed ratio of $CH_3OH$/EO/$CO_2$ (M:E:C) can be about 1:1:1. This feed ratio can facilitate water free pathway for DMC production. Additionally, the operational pressure of the reactor can be reduced from high pressure (beyond 100 bar) to low pressure (below 10 bar) without much compromise on DMC selectivity and $CO_2$ conversion. Therefore, this process not only converts $CO_2$, but also presents a cost effective route for DMC production.

This technology has been confirmed by calculations done based on thermodynamic GFEM principle as discussed above. These calculations identified optimal operating conditions in which the highest $CO_2$ and MeOH conversions could be achieved while achieving high yield DMC selectivity.

The conditions include, for example,

The variable feed composition of MeOH/$CO_2$ (M:C) ratio in the range of about 1:1 to about 4:1 at different temperatures and pressures in the range of 100° C. to 200° C. at 20 bar to 100 bar pressure;

Variable EO/MeOH (E:M) ratio in the range of about 0.25 to about 1.25 at stoichiometric feed ratio of MeOH/$CO_2$ (M:C) of about 2:1;

Variable Operational temperatures and pressures in the range of 50° C. to 200° C. and 1 bar to 100 bar respectively at a feed ratio of EO/MeOH/$CO_2$ (E:M:C) of about 1:1:1;

Overall study to maximize DMC selectivity and $CO_2$ conversion by varying EO/$CH_3OH$ ratio, MeOH/$CO_2$ (M:C) ratio at variable pressures in the range of 1 bar to 100 bar at a constant temperature of 100° C.; and Phase stability assessment to ensure homogeneity of the reaction species in a single phase during the reaction.

EXAMPLES

The inventors conducted various assessments starting from a base case model in which a stoichiometric feed composition was utilized and studied the impact of varying pressure and temperature on DMC yield, MeOH conversion and $CO_2$ conversion. Next, EO was introduced as a chemical scavenger to trap water in situ in the process while studying its effect on DMC yield, MeOH conversion and $CO_2$ conversion. Finally, the ratio of EO to MeOH and $CO_2$ was optimized to identify the point of maximum DMC yield, and feed conversion.

Base Case

Figure 2:
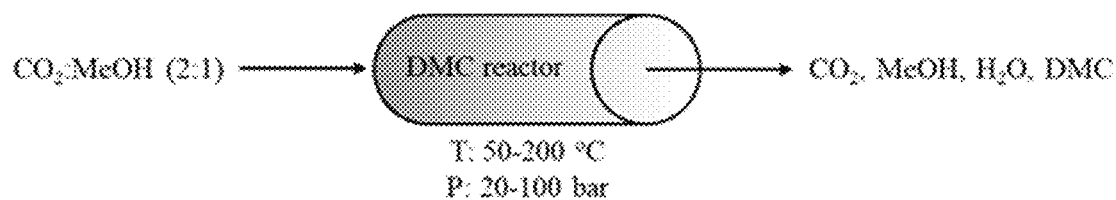
FIG. 2 is a block diagram of the base case scenario, wherein the reaction temperature varied from 50° C. to 200° C., and the pressure varied from 20 to 100 bar at the molar feed ratio of MeOH:CO$_2$(M:C)=2:1.

In the base case, a thermodynamic analysis of the impact of temperature was conducted, and pressure on product composition at stoichiometric feed ratio of MeOH:$CO_2$ (M:C)=2:1. In this analysis, reaction temperature was varied from 50° C. to 200° C., and pressure was varied from 20 bar to 100 bar. In terms of response, the MeOH conversion was calculated. A schematic of the reaction conditions and feed composition in block diagram form is provided below in FIG. 2.

Figure 3:
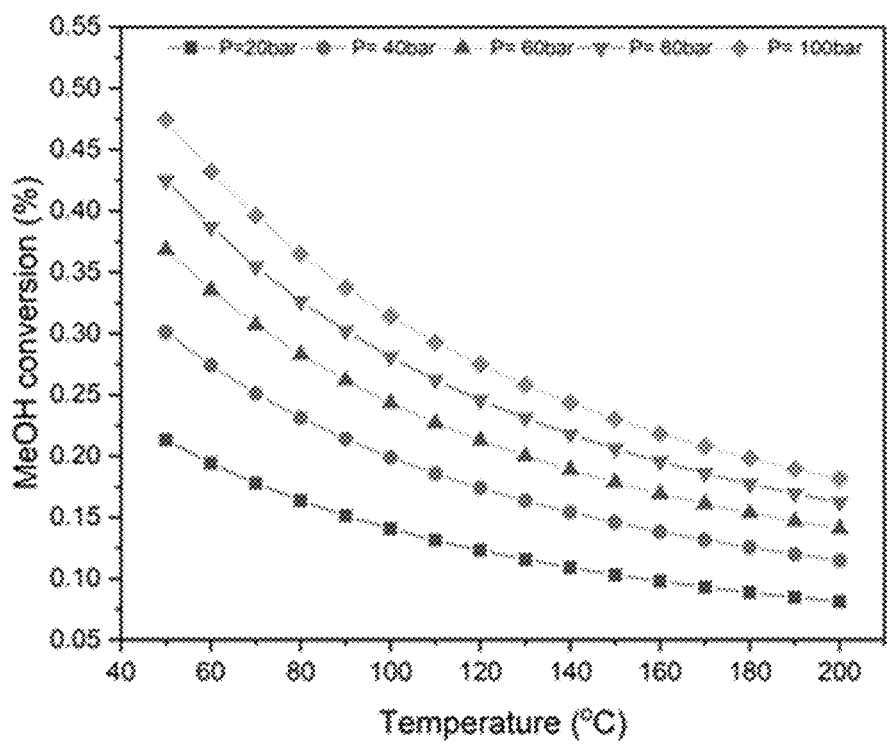
FIG. 3 is graphical illustration of the impact of variation of temperature and pressure on MeOH conversion. The molar feed ratio of MeOH to CO$_2$ (M:C) is set at a constant value of 2:1 in all cases.

FIG. 3 reports MeOH conversion for the different cases when both; temperature and pressure are varied. It can be seen that conversion of MeOH is very low (less than 1%) in all cases. However, the trend of conversion is observed to increase with increase in pressure and decrease in temperature in general. At a high pressure of 100 bar and a low temperature of 50° C., the conversion of MeOH is 0.47%, which indicates that the interplay of thermodynamic barriers have serious effect on conversions.

Variation of MeOH to $CO_2$ Ratio

Figure 4:
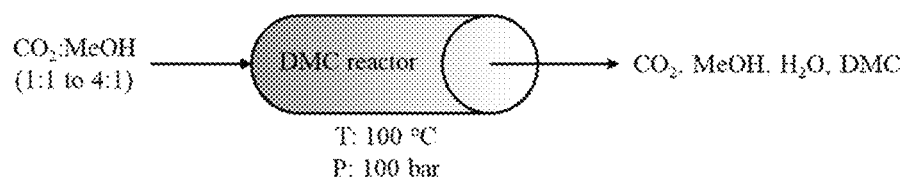
FIG. 4 is a block diagram for the case in which the effect of variation of molar feed ratio on conversions and product selectivity is studied, wherein the reaction temperature=100° C., and the pressure=100 bar at the molar feed ratio of MeOH:CO$_2$ (M:C) in the range of 1:1 to 4:1.

In this example, the impact of variation of MeOH to $CO_2$ ratio (in the range of 1:1 to 4:1) was demonstrated to identify its impact on conversion of MeOH. A block diagram of this scheme is provided in FIG. 4. The temperature and pressure conditions in this setup were fixed at 100° C. and 100 bar at all MeOH to $CO_2$ ratios.

Figure 5:
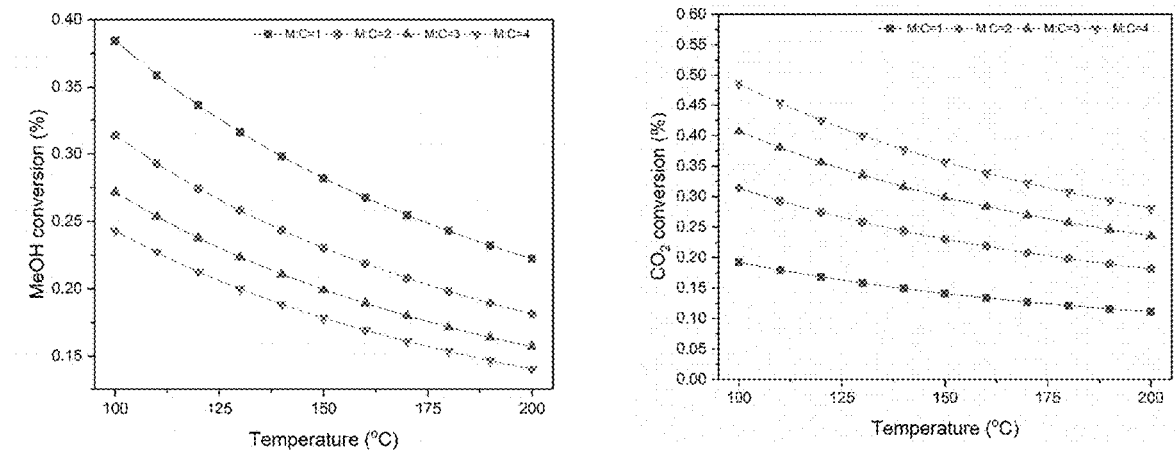
FIG. 5 is graphical illustration of the impact of variation of the MeOH to CO$_2$ (M:C) ratio in the range of 1 to 4 on (a) % MeOH conversion (b) % CO$_2$ conversion (c) DMC selectivity, the temperature=100° C., and the pressure=100 bar.
Figure 5:
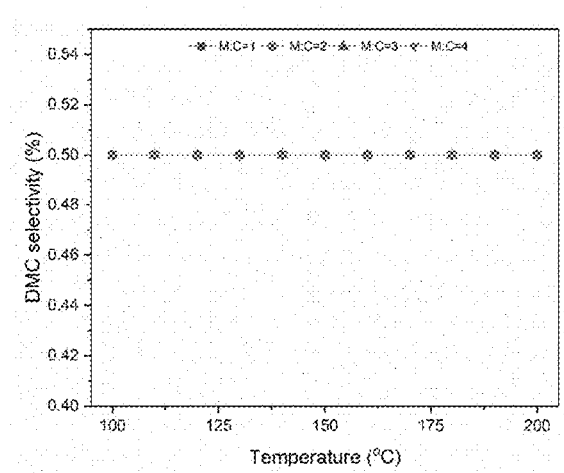

FIG. 5 provides a graphical illustration of the impact of variation of MeOH to $CO_2$ ratio (M:C) on % MeOH conversion, % $CO_2$ conversion and DMC selectivity. It can be observed that with increase in the concentration of MeOH from sub stoichiometric ratio of 1:1 to over-stoichiometric ratio of 4:1, the conversion of MeOH decreases to almost half the initial concentration of ~0.4%. However, the almost opposite effect is seen in terms of the conversion of $CO_2$, which is seen to increase by the same amount. Also, as the system transforms from $CO_2$ dominated system to MeOH dominated system, the interaction of each molecule of MeOH with $CO_2$ increases, resulting in higher $CO_2$ conversion. However, no effect of the variation of MeOH to $CO_2$ ratio is seen on the DMC selectivity as equal concentration of water and DMC is produced from the reaction. This indicates that water needs to be removed from the system to increase SDMC.

From this example, it can be inferred that high MeOH to $CO_2$ ratio is desirable for high $CO_2$ conversions, while low MeOH to $CO_2$ ratio is desirable for high MeOH conversion and there is no effect of variation of this parameter on DMC selectivity.

Variation of EO to MeOH Ratio

Figure 6:
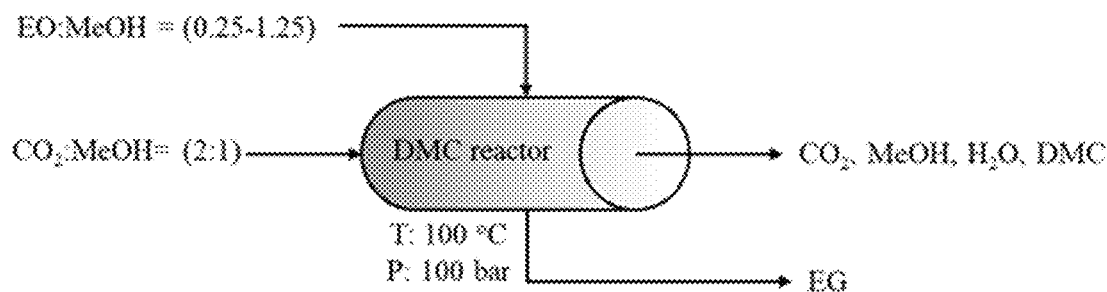
FIG. 6 is a block diagram for the case in which effect of variation of EO to MeOH (E:M) on conversions and product selectivity is studied, the reaction temperature=100° C., the pressure=100 bar, and MeOH:CO$_2$=2:1.

From the previous example of variation of MeOH to $CO_2$, it was observed that this ratio does not affect DMC selectivity. In this example, the inventors investigated the impact of removal of water by using chemical scavenger EO to realize if it could increase DMC selectivity. The block diagram in FIG. 6 illustrates this example.

In this example, the MeOH to $CO_2$ ratio is kept at its stoichiometric concentration, while temperature and pressure are also set to 100° C. and 100 bar that were found to be optimal from previous examples. Only the EO to MeOH ratio is varied to observe its impact on DMC selectivity, % MeOH conversion and % $CO_2$ conversion. The inventors recognized that EO will react with water in-situ in the reaction to produce EG, which itself is a water desiccant and will further remove water upon its formation.

Figure 7:
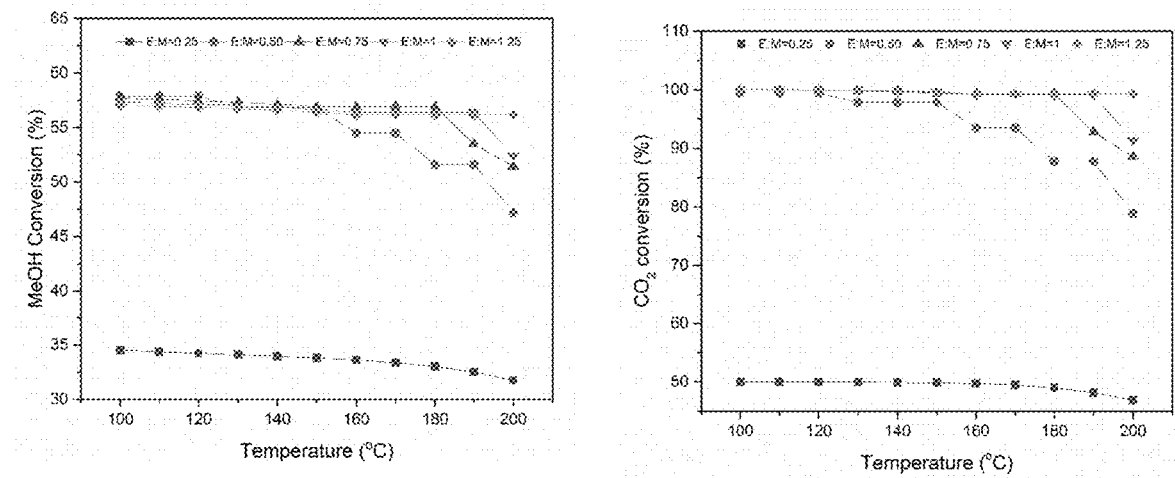
FIG. 7 is graphical illustration of the impact of variation of the MeOH to CO$_2$ (M:C) ratio in the range of 1 to 4 on (a) % MeOH conversion (b) % CO$_2$ Conversion (c) DMC Selectivity, temperature=100° C., and pressure=100 bar.
Figure 7:
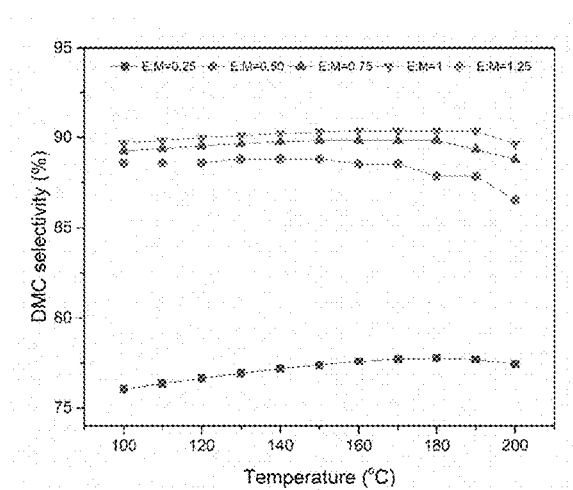

From FIG. 7, it can be seen that the immediate effect of addition of EO leads to drastic increase in both MeOH conversion and CO₂ conversion. Additionally, selectivity of DMC as a desirable product is also seen to increase from 50% to more than 70%. Since EO has high chemical affinity for reaction with water, the moment water is produced from the reaction of MeOH and CO₂, it reacts with EO to form EG as per the Eq. 3 below:

$$C_2H_4O + H_2O \rightarrow C_2H_6O_2 \quad (3)$$

Due to shift in equilibrium upon removal of water by formation of EO, higher conversions of both MeOH and CO₂ are realized. Also, the amount of water removal clearly depends on the concentration of EO in the reaction mixture. Low concentration of EO (low E:M ratio) results in low conversions and selectivity, for instance; E:M ratio of 0.25 results in only 35% and 50% conversion of MeOH and CO₂ respectively at a selectivity of DMC of 76%. Whereas, a higher concentration of 0.5 and above results in almost 57% conversion of MeOH and 99% conversion of CO₂ at an extremely high selectivity of DMC of 90%. This analysis therefore illustrates that an optimal ratio could be derived in terms of EO to MeOH ratio that could provide high conversion of both the reactants with high selectivity of DMC. The analysis at a fixed condition of 100° C. and 100 bar while varying E:M ratio indicates that an E:M ratio of 0.5 at stoichiometric feed ratio of MeOH and CO₂ provides a most optimal conversion of 57% and 99% in MeOH and CO₂, while a DMC selectivity of 88%.

Optimization of MeOH to CO₂ Ratio and EO to MeOH Ratio

Figure 8:
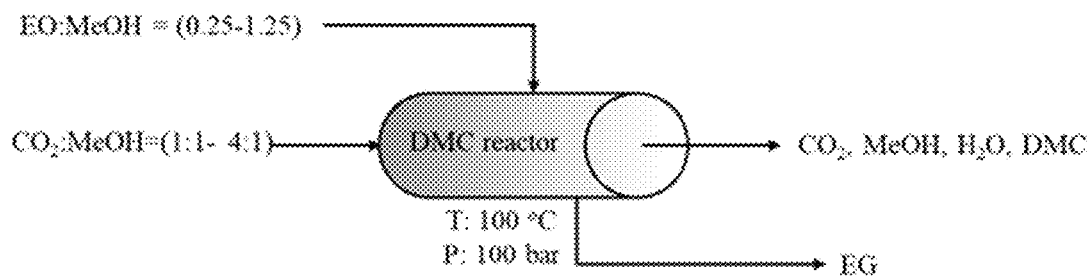
FIG. 8 is a block diagram for the case in which the effect of variation of both ratios of Ethylene Oxide to MeOH and MeOH to CO$_2$ on conversions and product selectivity is studied, Reaction temperature=100° C., and pressure=100 bar.

In this example, the impact was illustrated of variation of both, MeOH to CO₂ (M:C ratio) and EO to MeOH ratio on % CO₂ conversion, % MeOH conversion and DMC selectivity. In this analysis, the system temperature and pressure are kept at constant values of 100° C. and 100 bar respectively. FIG. 8 is the block diagram illustrating this study.

Figure 9:
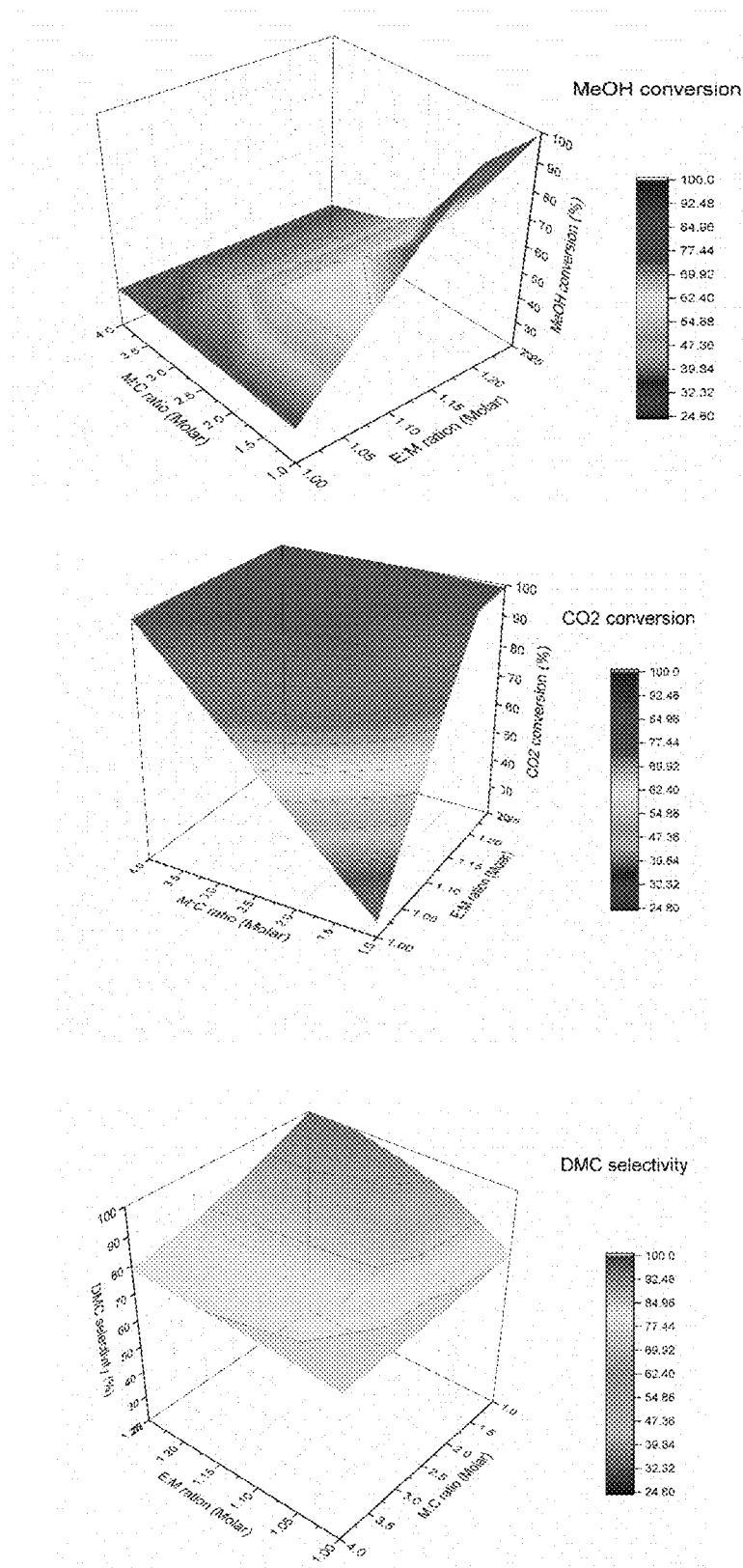
FIG. 9 is the three dimensional plots demonstrating the impact of simultaneous variation of M:C ratio (from 1 to 4) and E:M ratio (from 0.25 to 1.25) on (a) % MeOH conversion, (b) % CO$_2$ conversion, and (c) DMC Selectivity, system temperature=100° C., and pressure=100 bar.

In order to study the impact of relative concentration of MeOH, CO₂ and EO on product selectivity and feed conversions, the M:C ratio was varied from sub-stoichiometric condition of 1:1 to 4:1 and E:M ratio from 0.25 to 1.25 simultaneously. FIG. 9 is three-dimensional plots illustrating the impact of these parameters on the aforementioned target functions.

As can be seen from FIG. 9, high M:C ratio and low E:M ratio leads to lowest MeOH conversion and highest CO₂ conversions. However, at this condition, selectivity of DMC is at its lowest point. On the other hand, high E:M ratio leads to high conversions of both, MeOH and CO₂, along with high DMC selectivity. In particular, it can be observed that an E:M value of 1 to 1.5 and M:C value of 1 could be optimal to achieve highest conversion of >95% for both CO₂ and MeOH at a ~97% selectivity of DMC. This indicates that, if the molar composition of MeOH is 2 mole, then EO should be about 2 or 3 mole, while CO₂ should also be 2 mole. Also, it can be noted that there is no significant gain in CO₂ and MeOH conversion upon increasing the E:M ratio to 1.5 from 1, which indicates that E:M ratio of 1 could be just sufficient for achieving >95% conversions of both CO₂ and MeOH at high DMC selectivity of ~97%. Therefore, the most optimal condition for direct synthesis reaction in the presence of chemical scavenger EO could be MeOH:CO₂: EO (M:C:E) of 1:1:1.

Scope for Further Pressure Reduction

Figure 10:
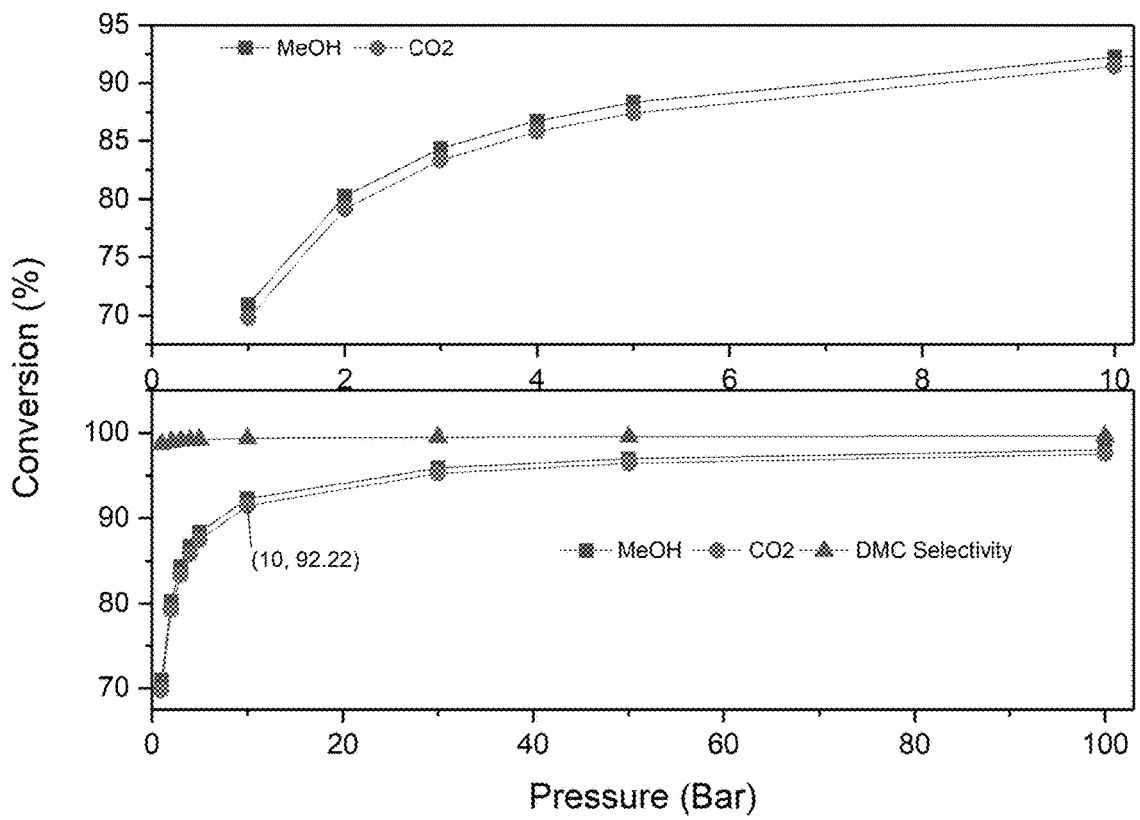
FIG. 10 illustrates the impact of pressure reduction from 100 bar to 1 bar on MeOH conversion, CO$_2$ conversion, and DMC selectivity at a constant feed ratio of MeOH:CO$_2$:EO (M:C:E)=1:1:1.

An illustration is provided of the scope for pressure reduction from 100 bar to a low pressure of 1 bar on the MeOH conversion. This study was operated at the optimal feed ratio of MeOH:CO₂:EO (M:C:E)=1:1:1 and 100° C., while we observe the impact of pressure reduction from 100 bar to 1 bar on MeOH conversion, CO₂ conversion and DMC selectivity. FIG. 10 illustrates this effect.

FIG. 10 shows that pressure reduction from 100 bar to 30 bar will not lead to significant changes in the conversions nor in the selectivity of DMC values. In addition to this, due to the presence of EO water scavenger and its reaction with water in situ, the selectivity towards DMC is extremely high at all pressure conditions. A close study on the conversion effect from pressure reduction from 30 bar to 10 bar also reveals that only a conversion decrease of 3-4% happens for both MeOH and CO₂, while DMC selectivity remains practically the same of >99%. This indicates that pressure is no longer a controlling parameter that drives the conversions in this reaction. If the pressure is reduced from 10 bar to 5 bar, further reduction of conversions happens up to an extent of 3-4% in both MeOH and CO₂, but not the selectivity of DMC. This means that there is a positive tradeoff in reduction of pressure from 10 bar to 5 bar as not much effect is observed in conversions and selectivity but leads to almost 50% feed compression cost (from 10 bar to 5 bar). Finally, a pressure change from 5 bar to 1 bar shows a drastic impact on conversions of both MeOH and CO₂ sliding it down to ~70% with a slight 0.5% decrease in DMC selectivity to 98.5%. This indicates that an optimal pressure point exists between 5 bar and 1 bar that acts as a tipping point leading to serious impact on conversion and selectivity. Nevertheless, 5 bar pressure serves to be a suitable pressure conditions that guarantees ~87% conversion of both MeOH and CO₂, while keeping selectivity of DMC at a high value of ~98%. The direct conversion reaction can be operated at the feed ratio of MeOH:CO₂:EO (M:C:E)=1:1:1 at a pressure of 5 bar. Pressure reduction from 100 bar to 5 bar can save at least 90% energy associated with the compression of feed gases and will lead to significant reduction in the cost of the desired product DMC making it cheaper or more competent to the commercial processes.

Phase Envelope Calculations

One of the operational concerns for any reaction is the stability of the phase of the reaction mixture as they may create undue transport challenges. If the reaction happens completely under one phase (homogeneous), then the effect of interfacial mass transfer resistances are nullified. In this work, since the species involved are in different phases (e.g., CO₂ is in vapor phase at 100° C.), a phase envelope calculation was performed to identify the regions of phase instability. This calculation was performed using ASPEN® Plus process simulator in which a Gibbs reactor was used at predefined conditions of temperature, pressure and feed composition governed by a sensitivity analysis tool. The approach involved varying temperature and pressure simultaneously, and recording the vapor fraction of the resultant product mixture. In particular, since the reaction involved operation from 100° C. to 200° C. temperature, and pressure from 1 bar to 100 bar, the simultaneous effect of these parameters were plotted to observe their impact on vapor fraction. Table 2 below illustrates the results of this sensitivity analysis.

Table 2 Sensitivity analysis results describing the phase of the reaction products as a function of temperature in the range of 50 to 200° C. and pressure in the range of 1 bar to 100 bar. Feed comprises of MeOH:CO₂:EO (M:C:E)=2:1:1

| Temperature (° C.) | P = 1bar | P = 12bar | P = 23bar | P = 34bar | P = 45bar | P = 56bar | P = 67bar | P = 78bar | P = 89bar | P = 100bar |
|---|---|---|---|---|---|---|---|---|---|---|
| 50 | 0 | 0 | 0 | 0 | 0 | 0 | 0 | 0 | 0 | 0 |
| 66.66667 | 0 | 0 | 0 | 0 | 0 | 0 | 0 | 0 | 0 | 0 |
| 83.33333 | 1 | 0 | 0 | 0 | 0 | 0 | 0 | 0 | 0 | 0 |
| 100 | 1 | 0 | 0 | 0 | 0 | 0 | 0 | 0 | 0 | 0 |
| 116.6667 | 1 | 0 | 0 | 0 | 0 | 0 | 0 | 0 | 0 | 0 |
| 133.3333 | 1 | 0 | 0 | 0 | 0 | 0 | 0 | 0 | 0 | 0 |
| 150 | 1 | 0 | 0 | 0 | 0 | 0 | 0 | 0 | 0 | 0 |
| 166.6667 | 1 | 1 | 0 | 0 | 0 | 0 | 0 | 0 | 0 | 0 |
| 183.3333 | 1 | 1 | 0.502466 | 0 | 0 | 0 | 0 | 0 | 0 | 0 |
| 200 | 1 | 1 | 1 | 0.634458 | 0 | 0 | 0 | 0 | 0 | 0 |

In this analysis, a constant feed composition of MeOH to $CO_2$ ratio of 2:1 was maintained, and the temperature was varied from 50° C. to 200° C. at different pressures in the range of 1 bar to 100 bar. The vapor fraction value of 1 indicates that the mixture is completely in vapor phase, while a value of 0 indicates that product mixture is completely in liquid phase. An intermediate value between 0 and 1 indicates a region of vapor-liquid equilibrium, which needs to be avoided. From Table 2, it can be observed that at a pressure beyond 34 bar, all the product mixtures will remain in liquid phase ensuring phase homogeneity. For the pressures in the range of 1 to 34 bar, vapor liquid transitions may happen. Since one of the optimal solutions from this work is at 5 bar condition, it is required to conduct a phase envelope calculation in a range of 1 to 10 bar pressure to identify the regions of phase instability. Table 3 provides phase data in this range of operation.

Table 3 Sensitivity analysis results describing the phase of the reaction products as a function of temperature in the range of 10 to 200° C., and pressure in the range of 1 bar to 10 bar. Feed comprises of MeOH:$CO_2$:EO (M:C:E)=2:1:1 incorporates implementation of a water scavenger that removes water in situ in the reaction to form a valuable product EG from EO:

1. A method to produce DMC from $CO_2$ and MeOH by the following:
   a. A reactor in which $CO_2$ and MeOH are added in parallel.
   b. Method stated in point (a) above, while the both the reactants $CO_2$ and MeOH are added in series.
   c. The reactor operates at a pressure range of 1 bar to 100 bar, wherein the reactants are first pressurized and fed to the reactor, or are pressurized within the reactor by an inert gas.
   d. The reactor operates in continuous mode which has the facility of continuous flow of feed into the reactor and products leaving the reactor.
   e. The reactor operates at a temperature of 100° C. to 200° C.
2. A method to remove byproduct water from the synthesis reaction that increases the conversion of feed comprising of MeOH and $CO_2$.

| Temperature (° C.) | P = 1bar | P = 2bar | P = 3bar | P = 4bar | P = 5bar | P = 6bar | P = 7bar | P = 8bar | P = 9bar | P = 10bar |
|---|---|---|---|---|---|---|---|---|---|---|
| 100 | 1 | 1 | 0 | 0 | 0 | 0 | 0 | 0 | 0 | 0 |
| 125 | 1 | 1 | 1 | 1 | 0.04549 | 0 | 0 | 0 | 0 | 0 |
| 150 | 1 | 1 | 1 | 1 | 1 | 1 | 1 | 1 | 1 | 0.143165 |
| 175 | 1 | 1 | 1 | 1 | 1 | 1 | 1 | 1 | 1 | 1 |
| 200 | 1 | 1 | 1 | 1 | 1 | 1 | 1 | 1 | 1 | 1 |

As shown in Tale 3, at a temperature of 175° C. and above, the product mixture is completely in vapor phase, indicating that the reaction would happen completely in a homogeneous vapor phase. On the other hand, for all the temperature conditions below 175° C., there is a possibility of phase split. Additionally, for pressure ranges from 3 bar to 10 bar at 100° C. temperature, a complete liquid phase is observed.

Figure 11:
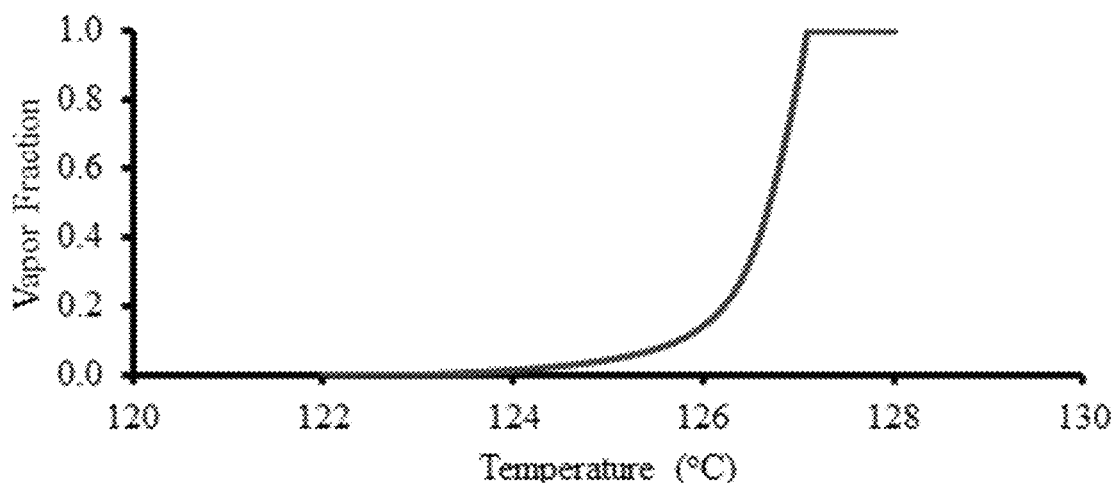
FIG. 11 shows the phase change of the reaction product mixture in the range of 122 to 128° C. at 5 bar at feed composition of MeOH:CO$_2$:EO (M:C:E)=2:1:1.

In order to clearly identify the actual phase split at 5 bar (which is the optimal condition from present analysis), the inventors conducted a sensitivity analysis by varying only the temperature at constant pressure of 5 bar to identify the region of phase split. FIG. 11 provides a phase split curve at 5 bar condition. It can be seen that the phase split only happens in the range of 122° C. to 128° C. temperature, and therefore ensures that all temperature conditions below this temperature at 5 bar will be completely in liquid phase.

In summary, provided herein is a novel method of circumventing thermodynamic barriers associated with direct synthesis of DMC process from $CO_2$ that result in low conversions of MeOH and $CO_2$. In particular, this method 3. Method stated in point 2 that involves addition of a water scavenger to remove water in situ in the reaction.
4. The method stated in point 3, wherein the scavenger is EO and serves as a means of enhancing the conversion of the feed by removal of one product (water) to push the reaction forward.
5. The ratio of EO to MeOH in particular is in the range of 0 to 4, wherein the ratio is preferably 1 to get highest conversion.
6. The ratio of MeOH to $CO_2$ stated above in point 5 is in the range of 0.5 to 4, wherein the highest conversion could be in the range of 0.5 to 1.5, while the most preferred ratio is at 1:1.
7. The most appropriate ratio of MeOH to $CO_2$ to EO is 1:1:1 to achieve highest conversion of >95% in MeOH and DMC selectivity of >95%. However, this ratio could be varied in any proportion with only condition that EO concentration should be sufficient to remove all water produced in the reaction.
8. The method stated in point 3, wherein the EO used in the process as water scavenger also serves as a source to produce EG as a byproduct in the reaction.

9. Method stated in point 8 could be an alternative method of producing EG utilizing the benefit of reaction symbiosis that also helps direct synthesis of DMC process by in situ water removal.
10. The optimal ratio reported in point 7 could be operated at a lower pressure up to 1 bar. With the most economically optimal ratio could be preferably below 10 bar (most preferably at 5 bar) conditions as approximately 85% to 92% thermodynamic conversions of the feed could be achieved around 10 bar condition.
11. The optimal ratio stated in point 10 could serve as method for reducing the compression cost by up to 90% by operating the reactor at below 10 bar rather than 100 bar in erstwhile processes.

As used herein and in the appended claims, the singular form of a word includes the plural, unless the context clearly dictates otherwise. Thus, the references "a," "an" and "the" are generally inclusive of the plurals of the respective terms. For example, reference to "an ingredient" or "a method" includes a plurality of such "ingredients" or "methods." The term "and/or" used in the context of "X and/or Y" should be interpreted as "X," or "Y," or "X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components. Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE CITATIONS

[1] B. A. V. Santos, V. M. T. M. Silva, J. M. Loureiro, and A. E. Rodrigues, "Review for the Direct Synthesis of Dimethyl Carbonate," *Chem Bio Eng Rev.*, vol. 1, no. 5, pp. 214-229, 2014.

[2] M. A. Pacheco and C. L. Marshall, "Reviews Review of Dimethyl Carbonate (DMC) Manufacture and Its Characteristics as a Fuel Additive," 1997.

[3] M. Honda, M. Tamura, Y. Nakagawa, S. Sonehara, K. Suzuki, K. Fujimoto, and K. Tomishige, "Ceria-Catalyzed Conversion of Carbon Dioxide into Dimethyl Carbonate with 2-Cyanopyridine," *Chem Sus Chem*, vol. 6, no. 8, pp. 1341-1344, 2009.

[4] J.-C. Choi, L.-N. He, H. Yasuda, and T. Sakakura, "Selective and high yield synthesis of dimethyl carbonate directly from carbon dioxide and MeOH," *Green Chem.*, vol. 4, no. 3, pp. 230-234, 2002.

[5] H. Seung Tae, P. Hyung Sang, L. Jong Sung, L. Youn-Woo, A. Masakazu, and K. Jae-Duck, "Synthesis of dimethyl carbonate from MeOH and supercritical carbon dioxide," *Res. Chem. Intermed.*, vol. 32, no. 8, pp. 737-747, 2006.

[6] Q. Cai, B. Lu, L. Guo, and Y. Shan, "Studies on synthesis of dimethyl carbonate from MeOH and carbon dioxide," *Catal. Commun.*, vol. 10, no. 5, pp. 605-609, January 2009.

[7] S. Fang and K. Fujimoto, "Dioxide and MeOH Catalyzed By Base," *Appl. Catal. A Gen.*, vol. 142, pp. L1-L3, 1996.

[8] K. Kohno, J. C. Choi, Y. Ohshima, H. Yasuda, and T. Sakakura, "Synthesis of dimethyl carbonate from carbon dioxide catalyzed by titanium alkoxides with polyether-type ligands," *Chem Sus Chem*, vol. 1, no. 3, pp. 186-188, 2008.

[9] Y. Saito, M. Okano, T. Sako, J.-C. Choi, and T. Sakakura, "Selective Conversion of Carbon Dioxide to Dimethyl Carbonate by Molecular Catalysis," *J. Org. Chem.*, vol. 63, no. 20, pp. 7095-7096, 2002.

[10] J.-C. Choi, L.-N. He, H. Yasuda, and T. Sakakura, "Selective and high yield synthesis of dimethyl carbonate directly from carbon dioxide and MeOH," *Green Chem.*, vol. 4, no. 3, pp. 230-234, 2002.

[11] K. Kohno, J. C. Choi, Y. Ohshima, A. Yili, H. Yasuda, and T. Sakakura, "Reaction of dibutyltin oxide with MeOH under $CO_2$ pressure relevant to catalytic dimethyl carbonate synthesis," *J. Organomet. Chem.*, vol. 693, no. 7, pp. 1389-1392, 2008.

[12] D. Ballivet-Tkatchenko, S. Chambrey, R. Keiski, R. Ligabue, L. Plasseraud, P. Richard, and H. Turunen, "Direct synthesis of dimethyl carbonate with supercritical carbon dioxide: Characterization of a key organotin oxide intermediate," *Catal. Today*, vol. 115, no. 1-4, pp. 80-87, 2006.

[13] A. Bansode and A. Urakawa, "Continuous DMC synthesis from $CO_2$ and MeOH over a CeO2 catalyst in a fixed bed reactor in the presence of a dehydrating agent," *ACS Catal.*, vol. 4, no. 11, pp. 3877-3880, 2014.

[14] D. Stoian, F. Medina, and A. Urakawa, "Improving the Stability of CeO2 Catalyst by Rare Earth Metal Promotion and Molecular Insights in the Dimethyl Carbonate Synthesis from CO2 and MeOH with 2-Cyanopyridine," *ACS Catal.*, vol. 8, no. 4, pp. 3181-3193, 2018.

[15] Siemens Industry, "Process Analytics in Ethylene Oxide and Ethylene Glycol Plants Ethylene Oxide and Ethylene Glycols," *Analytical products*, no. PIACS-00013-1015, 2015.

[16] A. G. Daful, "Simulation of Reactive Distillation: Comparison of Equilibrium and Nonequilibrium Stage Models," *Int. J. Chem. Mol. Nucl. Mater. Metall. Eng.*, vol. 6, no. 10, pp. 33-47, 2000.

[17] Z. Huang, J. Li, L. Wang, H. Jiang, and T. Qiu, "Novel Procedure for the Synthesis of Dimethyl Carbonate by Reactive Distillation," 2014.

[18] X. Hu, H. Cheng, X. Kang, L. Chen, X. Yuan, and Z. Qi, "Analysis of direct synthesis of dimethyl carbonate from MeOH and $CO_2$ intensified by in-situ hydration-assisted reactive distillation with side reactor," *Chem. Eng. Process.—Process Intensif.*, vol. 129, no. May, pp. 109-117, 2018.

[19] M. S. Challiwala, M. M. Ghouri, P. Linke, M. M. El-Halwagi, and N. O. Elbashir, "A combined thermo-kinetic analysis of various methane reforming technologies: Comparison with dry reforming," *J. CO2 Util.*, vol. 17, pp. 99-111, 2017.

[20] M. S. Challiwala, B. A. Wilhite, M. M. Ghouri, and N. O. Elbashir, "Multidimensional modeling of a microfibrous entrapped cobalt catalyst Fischer-Tropsch reactor bed," *AIChE J.*, vol. 64, no. 5, pp. 1723-1731, 2018.

The invention claimed is:

1. A method to produce DMC, the method comprising:
adding to a reactor reactants comprising $CO_2$ and MeOH for a first reaction,
wherein a pressure in the reactor is from 1 bar to 100 bar, a temperature in the reactor is from 100° C. to 200° C., the reactor operates in a continuous mode with a continuous flow of feed of the reactants into the reactor and products leaving the reactor, wherein the method further includes removing byproduct water, thereby increasing conversion of the feed by adding a water scavenger to the reactor to remove water in situ in the reactor in a second reaction, and
wherein a feed ratio of the MeOH to the $CO_2$ to the water scavenger is about 1:1:1.

2. The method of claim 1, wherein the water scavenger comprises EO.

3. A method to produce DMC, the method comprising:
adding to a reactor reactants comprising $CO_2$ and MeOH for a first reaction,
wherein a pressure in the reactor is from 1 bar to 100 bar, a temperature in the reactor is from 100° C. to 200° C., the reactor operates in a continuous mode with a continuous flow of feed of the reactants into the reactor and products leaving the reactor, wherein the method further includes removing byproduct water, thereby increasing conversion of the feed by adding a water scavenger to the reactor to remove water in situ in the reactor in a second reaction, and
wherein a feed ratio of the water scavenger to the MeOH is from about 0.5 to about 4.

4. The method of claim 3, wherein the feed ratio of the water scavenger to the MeOH is from about 0.5 to about 1.5.

5. The method of claim 2, wherein the pressure in the reactor is about 10 bar.

6. The method of claim 5, wherein conversion of the feed is about 85% to 92%.

7. The method of claim 2, wherein the pressure in the reactor is below 10 bar.

8. The method of claim 2, wherein the pressure in the reactor is about 5 bar.

9. The method of claim 2, wherein the pressure in the reactor is up to 1 bar.

10. The method of claim 9, wherein conversion of the MeOH is in the range of 1-99.9%.

11. The method of claim 9, wherein DMC selectivity is in the range of 1-99.9%.

12. The method of claim 2, wherein the second reaction is $EO+H_2O \rightarrow EG$.

13. The method of claim 1, further comprising pressurizing the $CO_2$ and the MeOH before or after being added to the reactor.

14. The method of claim 1, wherein the first reaction is $CO_2 + 2\ MeOH \rightarrow DMC + H_2O$.

15. The method of claim 1, wherein the first reaction and the second reaction occur in a single reactor thereby producing DMC at a conversion of MeOH and $CO_2$ at greater than 90% and a selectivity of DMC at greater than 90%.

16. The method of claim 3, wherein the first reaction and the second reaction occur in a single reactor thereby producing DMC at a conversion of MeOH and $CO_2$ at greater than 90% and a selectivity of DMC at greater than 90%.

17. The method of claim 3, wherein the water scavenger comprises EO.

* * * * *